United States Patent [19]

Oritani et al.

[11] Patent Number: 5,244,487
[45] Date of Patent: Sep. 14, 1993

[54] ADENINE DERIVATIVES AND THEIR USE AS AGENTS FOR INCREASING YIELD OF CROPS

[75] Inventors: Takashi Oritani, Toyama; Mitsunori Oda, Niigata; Taketo Maruyama, Niigata; Takashi Suzuki, Niigata; Akinori Tanaka, Niigata; Toshio Kajita, Narashino; Shigeo Yoshinaka, Niigata; Masakazu Furushima, Nagareyama, all of Japan

[73] Assignee: Mitsubishi Gas Chemical Co., Inc., Tokyo, Japan

[21] Appl. No.: 653,643

[22] Filed: Feb. 11, 1991

Related U.S. Application Data

[63] Continuation-in-part of Ser. No. 499,592, Mar. 26, 1990, abandoned.

[30] Foreign Application Priority Data

Mar. 28, 1989 [JP] Japan .................................. 1-73762
Sep. 22, 1989 [JP] Japan ................................. 1-244919

[51] Int. Cl.$^5$ ..................... A01N 43/90; A01N 43/54; C07D 473/34
[52] U.S. Cl. .................................... 504/241; 544/277
[58] Field of Search ............................. 544/277; 71/92

[56] References Cited

FOREIGN PATENT DOCUMENTS 073763  3/1989  Japan .

Primary Examiner—Mukund J. Shah
Assistant Examiner—Matthew V. Grumbling
Attorney, Agent, or Firm—Wyatt, Gerber, Burke and Badie

[57] ABSTRACT

Disclosed are novel adenine derivatives represented by the formula I and agriculturally acceptable acid addition salts thereof represented by the formula:

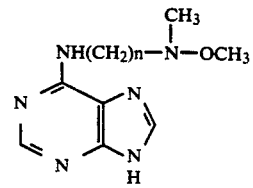

wherein n is an integer of 2–4.

Compositions for increasing yield of crops such as leguminous crops and gramineous crops which contain the above adenine derivatives or salts thereof as an active ingredient and methods for increasing yield of crops using these compositions are also disclosed.

17 Claims, 5 Drawing Sheets

ADENINE DERIVATIVES AND THEIR USE AS AGENTS FOR INCREASING YIELD OF CROPS

RELATED APPLICATION

This application is a continuation in part application of copending application Ser. No. 499,592 filed Mar. 26, 1990, now abandoned.

BACKGROUND OF THE INVENTION

The present invention relates to novel adenine derivatives represented by the following formula and agriculturally acceptable acid addition salts thereof, to compositions containing such compounds and to their use as agents for increasing yield of crops.

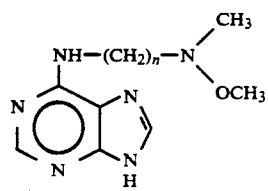

(wherein n is an integer of 2-4)

Hitherto, many substances have been found for adjustment of growth of plants such as crops, fruits and vegetables. Among them, those which belong to a group of substances generically called cytokinin-active substances are known to have many useful physiological activities. Representative compounds are zeatin, kinetin and 6-benzylaminopurine (hereinafter referred to as benzyladenine).

Such cytokinin-active substances have been known to have various useful properties for plants such as the control of growth by cell division in callus and intact plants, the promotion of buds and flower formation, the stimulation of seed germination, the overcoming of dormant phase of seeds, storage organs and buds, the promotion of sideshoot formation, and the retardation of the ageing processes in plants.

Several substances which show cytokinin activity have occur naturally, but such naturally occurring substances are available only in limited quantities and are difficult to obtain. In addition to those natural cytokinins, various synthetic adenine derivatives have been shown to have cytokinin activity. However, their practical use is quite limited. One of the reasons for such limitation is that both natural and synthetic cytokinins are poor in water-solubility and absorption into plants with the result that translocation to the organs is insufficient.

Previously, various studies have been made for increasing the yield of cereal crops such as waterfield rice plants and beans, but few of them have been practically applied in spite of many efforts.

It is an object of the present invention to provide active ingredients which are higher in water-solubility than conventional cytokinin-active substances, rich in physiological activity for practical use and not difficult to manufacture.

It has been known that cytokinins such as kinetin, zeatin, benzyladenine and thidiazuron have activities such as the control of growth by cell division in callus and intact plants, the differentiation of plant tissues, the stimulation of seed germination and senescence retardation. Recently, an attempt has been made to increase yield of cereal crops such as waterfield rice plants with the above-mentioned cytokinins. For example, it is reported in "Japanese Journal of Crop Science", Vol. 51, Extra issue 1, 1982, page 147-148 that zeatin and abscisic acid increase the ripening rate and thousand-kernel weight of husked rice according to the experiments of direct injection of these plant hormones into ears of rice plant. More recently, Japanese Patent Kokai No. 63-181933 discloses that yield of gramineous crops can be increased by treating ears with benzyladenine, thidiazuron, kinetin or zeatin.

Natural cytokins such as zeatin and ribosylzeatin are difficult of manufacture. Benzyladenine kinetin and thidiazuron can be synthesized with relative ease, but have low water-solubility and manifest poor absorption into plants and translocation to other organs. Thus, these are not efficient for practical use.

As a result of extensive and intensive research conducted by the inventors in view of the problems cited above, it has been found that adenine derivatives having a side chain represented by the following formula (A) substituted on the $N^6$ nitrogen atom of adenine and salts thereof are effective for attaining the above object. The present invention is based on such new finding.

Formula (A):

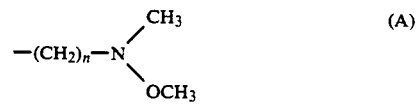

(A)

It has also been found that among these adenine derivatives and salts thereof, $N^6$-[2-(N-methoxy-N-methylamino) ethyl]adenine and its salts exhibit especially strong cytokinin activity.

The inventors have studied the activity of $N^6$-[2-(N-methyoxy-N-methylamino)-ethyl]adenine and salts thereof on plants and have found that these compounds not only have strong cytokinin activity but also increase the yield of agricultural crops when applied to leaves and stems of leguminous plants and cereal plants such as gramineous plants.

The present invention is based on these new findings.

SUMMARY OF THE INVENTION

The present invention relates to novel adenine derivatives and agriculturally acceptable acid addition salts thereof. These compounds are high in water-solubility, show excellent cytokinin activity, and therefore are useful for regulation of physiological activity of plants such as the control of growth by cell division in callus and intact plants, the promotion of buds and flower formation, the stimulation of seed germination, the overcoming of dormant phase of seed, storage organs and buds, the promotion of sideshoot formation, and the retardation of the ageing process inplants. Furthermore, the present invention relates to compositions, which contain amounts of such novel adenine derivatives which are effective for increasing yield of crops together with a agriculturally effective carrier, and to a method for increasing the yield of crops.

DESCRIPTION OF THE INVENTION

Figure 1:
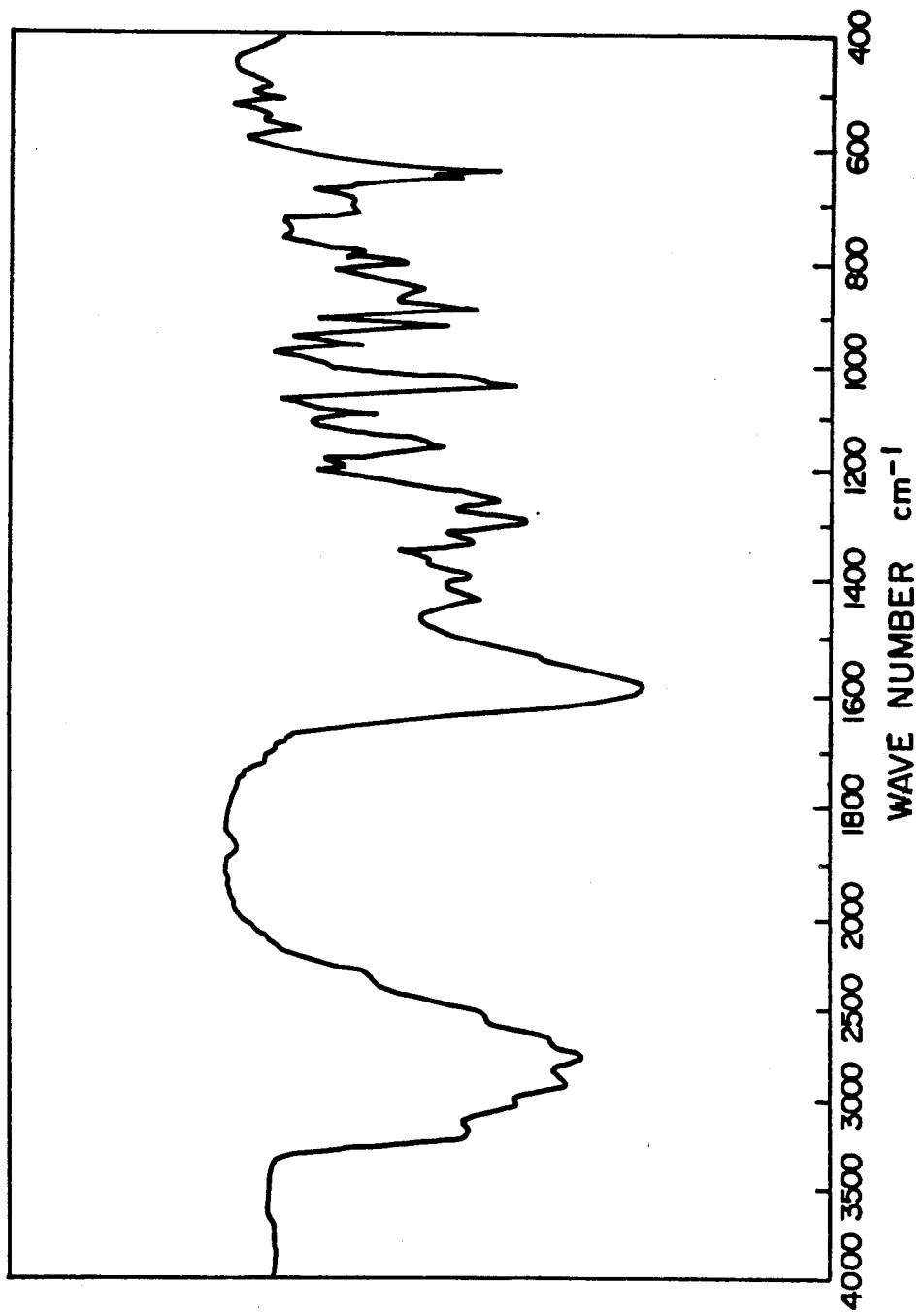
FIG. 1, FIG. 2 and FIG. 3 show IR absorption spectra of $N^6$-[2-(N-methoxy-N-methylamino)ethyl]adenine, $N^6$-[3-(N-methoxy-N-methylamino)propyl]adenine, and $N^6$-[4-(N-methoxy-N-methylamino)butyl]adenine of the present invention, respectively.

The present invention relates to adenine derivatives represented by the following formula and acid addition salts thereof:

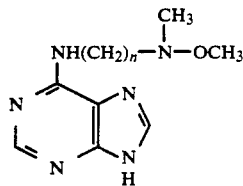
(I)

(wherein n is an integer of 2 to 4).

Suitable acid addition salts include, for example, those prepared from hydrochloric acid, sulfuric acid, nitric acid, phosphoric acid, formic acid or acetic acid. Other organic and inorganic acids may also be employed.

Furthermore, the present invention relates to compositions for increasing yield of crops, such compositions containing $N^6$-[2-(N-methoxy-N-methylamino)ethyl]adenine or other compounds of the invention as an active ingredient.

$N^6$-[2-(N-methoxy-N-methylamino)ethyl]adenine (sometimes referred to as "MAED" hereinafter) has the following structural formula:

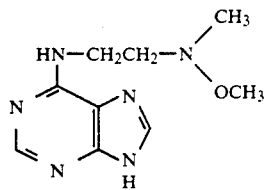

MAED easily forms acid additons salts with acids such as hydrochloric acid, sulfuric acid, nitric acid, phosphoric acid, formic acid and acetic acid. Such salts are sometimes generically referred to as "MAED's" hereinafter.

The adenine derivatives of the invention may be prepared, for example, by allowing 6-chloropurine to react with the diamine derivatives presented by the following formula (B) in an organic solvent such as alcohol in the presence of a trialkylamine such as ethyldiisopropylamine with heat.

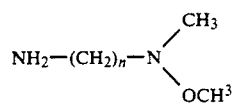

(wherein n is integer of 2 to 4).

In order to obtain the adenine derivatives in high purity, it is important to prepare the diamine derivatives in high purity. These pure diamine derivatives may be prepared by reacting N,O-dimethylhydroxylamine with N-(haloalkyl)phthalimide to give the phthalimide derivative of the diamine and thereafter deprotecting phthalimide to give the diamine derivative. It is possible to allow the isolated diamine derivative or the crude diamine derivative to react with 6-chloropurine.

Typical examples of the adenine derivatives of the invention are $N^6$-[2-(N-methoxy-N-methylamino)ethyl]adenine represented by the formula (1) $N^6$-[3-(N-methoxy-N-methylamino)propyl]adenine represented by the formula (2) and $N^6$-[4-(N-methoxy-N-methylamino)butyl]adenine represented by the formula (3).

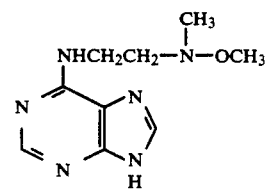
(1)

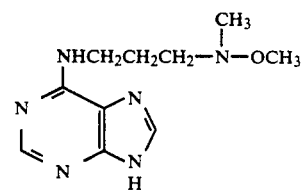
(2)

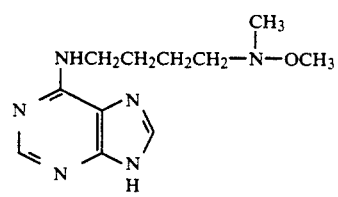
(3)

The adenine derivatives of the present invention can be converted to acid addition salts by reaction with mineral acids, such as hydrochloric acid, sulfuric acid, nitric acid or phosphoric acid or salts with organic acids such as formic acid or acetic acid by conventional procedures.

Typical salts of the invention include the hydrochloride of $N^6$-[2-(N-methoxy-N-methylamino) ethyl]adenine represented by the following formula (4):

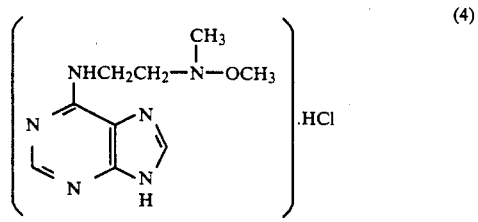
(4)

MEAD's per se can be used alone or as the active ingredient in a composition for increasing yield of crops. Typically, they are used in combination with agriculturally acceptable liquid or solid carriers and, optionally, with surface active agents as emulsifiers, dispersants, spreaders, and stickers such as those which are generally used in the field of formulation of agrochemicals.

Examples of formulations within the scope of the invention are emulsifiable concentrates, wettable powders, dusts and liquids.

As diluents for preparation of a liquid formulation, mention may be made of polar solvents such as alcohols, e.g., methanol and ethanol, water, dimethylformamide and dimethylsulfoxide.

As carriers for preparation of a wettable powder, granule or dust, there may be used talc, clay, bentonite, kaolin, montmorilonite, diatomaceous earth, phenol resin and white carbon.

Typical examples of surface-active agents which may be usefully employed in the practice of the invention are anionic surface-active agents such as sodium alkylbenzene-sulfonates and sodium laurylsulfate, cationic surface-active agents such as stearyltrimethylammonium chloride and nonionic surface-active agents such as polyoxyethylenealkylphenyl ether.

As dispersants, there may be used, in addition to the above surface-active agents, for example, sodium ligninsulfonate, methyl cellulose, and sulfite waste liquor.

As stickers i.e. materials to adhere the active agents to the plants, there may be used, for example, casein lime, glue, carboxymethyl cellulose, sodium alginate and polyvinyl alcohol.

Increase of crop yield can be attained by applying the derivatives or compositions containing an effective amount of at least one of them to the plants.

The site of application to the plants, the dosage and application time of the agents of the present invention may vary depending on the kind of plants as will be recognized by the skilled artisan. Effective amounts for increasing the yield of specific plants can be readily determined by standard procedures which will be readily apparent to those skilled in the art.

Typical examples of the plants to which the agents of the present invention may be usefully applied are leguminous crops such as soybean, red bean, kidney bean (Phaseolus vulgaris), winged bean (Psophocarpus) and peanut and gramineous crops such as rice, wheat, barley, rye, pearl barley, oat and maize.

The adenine derivatives and salts thereof of the present invention show excellent cytokinin activity, are high in water-solubility and can be employed as a cytokinin substance for a wide variety of agricultural utilities and for media of plant tissue culture.

The agents of the invention are remarkably effective to increase yield of crops, especially cereal crops.

The present invention is further explained by the following nonlimiting examples.

EXAMPLE 1

Preparation of $N^6$-[2-(N-methoxy-N-methylamino) ethyl]adenine of the formula (2):

First, a side chain amine was prepared and then was allowed to react with 6-chloropurine in the following manner.

(1) Preparation of $N^6$-[2-(N-methoxy-N-methylamino) ethyl]phthalimide:

To a suspension of 50 ml of isopropanol containing N,O-dimethylhydroxylamine hydrochloride (3.90 g, 40.0 mmol) was added dropwise 5.56 ml of triethylamine. The resulting mixture became homogeneous after 5 minutes. Thereto was added 2.45 g (10.0 mmol) of N-(bromoethyl)phthalimide and the mixture was refluxed for 29 hours. This was cooled to room temperature, then poured into 200 ml of a saturated aqueous solution of sodium bicarbonate and extracted with chloroform. The organic layer was separated and was washed with water and dried over magnesium sulfate. Chloroform was distilled off and the residue was purified by column chromatography on silica gel. Development with 30% hexane-chloroform resulted in elution of 1.37 g of N-(2-chloroethyl)-phthalimide and further development with chloroform resulted in 0.964 g (yield: 41%) of white cyrstals of N-[2-(N-methoxy-N-methylamino)ethyl]phthalimide.

Melting point: 130°–132° C.

$^1$H-NMR (60 MHz, CDC$_3$); =2.40 (s, 3H), 2.93(t, J=6H$_z$, 2H), 3.53 (s, 3H), 3.93(t, J=6H$_z$, 2H), 7.77 (m, 4H) ppm.

(2) Preparation of $N^6$-[2-(N-methoxy-N-methylamino)ethyl]adenine by deprotection of the imide, followed by condensation of 6-chloropurine:

In ethanol was dissolved 0.89 g (3.71 mmol) of the imide obtained in the above (1) and thereto was added 0.204 g (4.08 mmol) of hydrazine hydrate, followed by refluxing for 3 hours and cooling in an ice bath. The resulting solid was filtered off and the filtrate was concentrated to 2 ml by an evaporator with a water bath at 5° C. This concentrated solution was mixed with 5 ml of n-butanol and to the mixture were added 0.200 g (4.2 mmol) of 6-chloro-purine and 0.4 ml (4.2 mmol) of ethyldiisopropylamine and the mixture was gently refluxed for 5 hours. This was cooled to room temperature and then the solvent was distilled off under reduced pressure. The residue was purified by column chromatography on silica gel (eluent: chloroform/ethanol=95/5) to give 0.210 g (yield: 25%) of white crystals of $N^6$-[2-(N-methoxy-N-methylamino) ethyl]adenine.

Melting point: 168°–170° C.

Elemental analysis: Molecular formula: $C_9H_{14}N_6O$. Calculated values: C; 48.63, H; 6.34, N; 37.81 Found: C; 48.51, H; 6.11, N; 38.10.

$^1$H-NMR (60 MH$_z$, CDC$_3$); =2.67 (s, 3H), 2.78 (t, J=6H$_z$, 2H), 3.56 (s, 3H), 2.74 (t, J=6H$_z$, 2H), 8.05 (s, 1H), 8.12 (s, 1H) ppm.

IR absorption spectrum (KBr method) is shown in FIG. 1.

$_{max}$=3350$^s$, 1630$^s$, 1090$^s$cm$^{-1}$.

UV absorption spectrum; max=(H$_2$O), 207, 267 nm (0.1 N—HC ), 275 nm (0.1 N-NaOH), 274 nm, 282$^{sh}$nm.

EXAMPLE 2

Preparation of $N^6$-[2-(N-methoxy-N- methylamino)-propyl]adenine of the formula (3):

First, a side chain amine was prepared and then was allowed to react with 6-chloropurine in the following manner.

(1) Preparation of $N^6$-[2-(N-methoxy-N-methylamino)-propyl]phthalimide:

To a suspension of 50 mol of isopropanol containing N,O-dimethylhydroxylamine hydrochloride (3.97 g, 40.0 mmol) was added dropwise 5.56 ml of triethylamine. After 5 minutes, there was added 2.68 g (10.0 mmol) of N-(3-bromopropyl)phthalimide and the mixture was refluxed for 33 hours. This was cooled to room temperature, then poured into 200 ml of saturated aqueous solution of sodium bicarbonate and extracted with chloroform. The organic layer was separated and was washed with water and dried over magnesium sulfate. Chloroform was distilled off and the residue was purified by column chromatography on silica gel. Development with 30% hexane-chloroform resulted in elution of 1.03 g of N-(3-chloropropyl)phthalimide and further development with chloroform resulted in 1.21 g (yield: 53%) of white crystals of N-[3-(N-methoxy-N-methylamino)propyl]-phthalimide.

Melting point: 55°–57° C.

$^1$H-NMR (60 MHz, CDC$_3$); =1.93 (quin, J=6H$_z$, 2H), 2.55 (s, 3H), 2.68 (t, J=6H$_z$, 2H), 3.52 (s, 3H), 2.08 (t, J=6H$^z$, 2H), 7.75 (m, 4H) ppm.

(2) Preparation of N$^6$-[3-(N-methoxy-N-methylamino)-propyl]adenine by deprotection of the imide, followed by condensation with 6-chloropurine:

In 15 ml of ethanol was dissolved 1.21 g (4.88 mmol) of the imide obtained in the above (1) and there was added 0.293 g (5.86 mmol) of hydrazine hydrate, followed by refluxing for 6 hours and cooling in an ice bath. The resulting solid was filtered off and the filtrate was concentrated to 2 ml by evaporator with a water bath at 5° C. This concentrated solution was mixed with 6 ml of n-butanol and to the mixture were added 0.528 g (3.42 mmol) of 6-chloropurine and 0.68 ml of ethyldiisopropylamine and the mixture was gently refluxed for 5 hours. This was cooled to room temperature and then the solvent was distilled off under reduced pressure. The residue was purified by column chromatography on silica gel (eluent: chloroform/ethanol=9/1) to give 0.421 g (yield: 36%) of white crystals of N$^6$-[3-(N-methoxy-N-methylamino)propyl]adenine.

Melting point: 183°–185° C.

Elemental analysis: Molecular formula: C$_{10}$H$_{16}$N$_6$; Calculated values: C; 50.83, H; 6.83, N; 35.57; Found: C; 51.02, H; 6.79, N; 35.29.

$^1$H-NMR (60 MHz, CDC$_3$); =1.96 (quin, J=7H$_z$, 2H), 2.59 (s, 3H), 2.79 (t, J=7H$_z$, 2H), 3.53 (s, 3H), 3.71 (t, J=7Hz, 2H).

Figure 2:
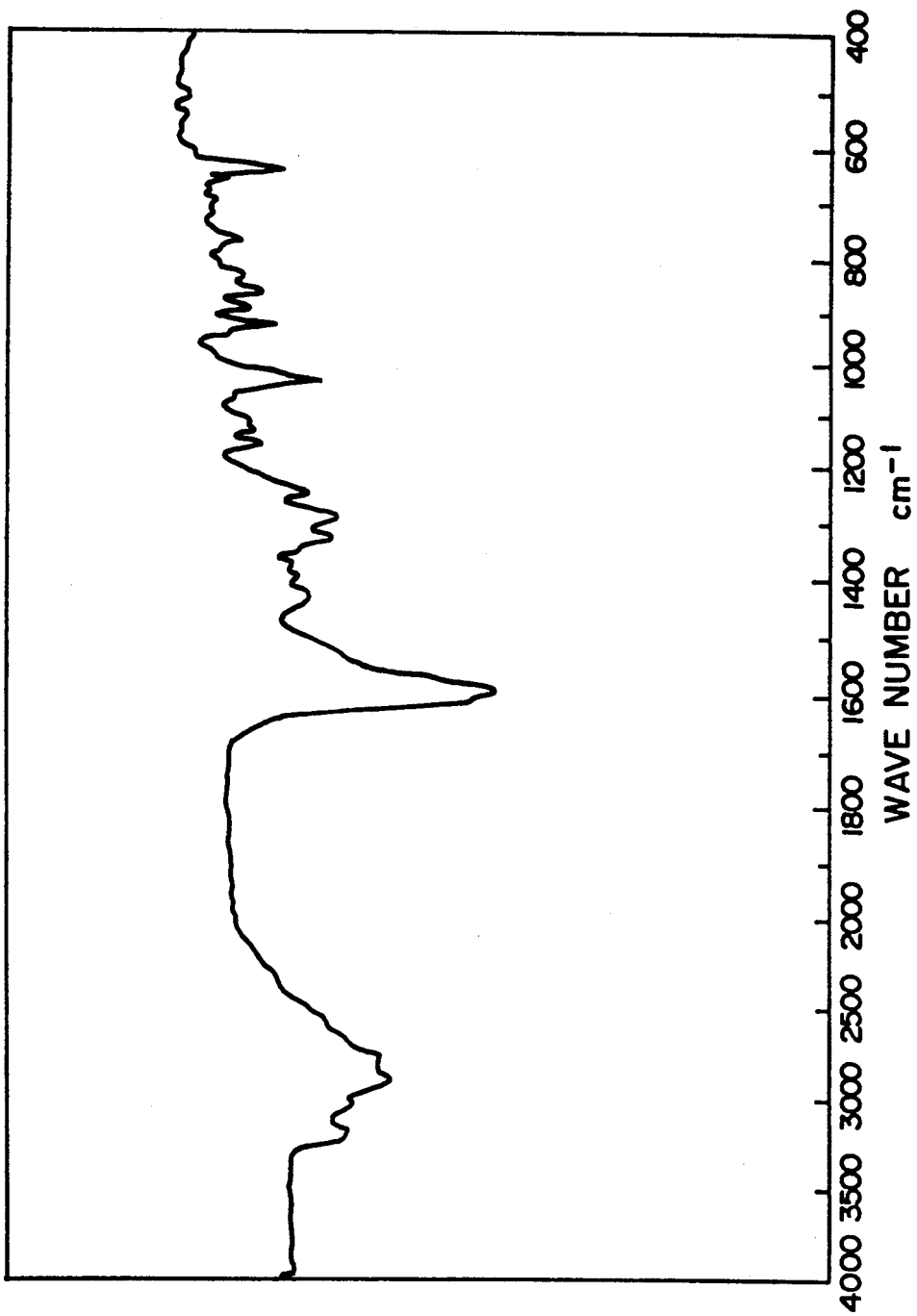

IR absorption spectrum (KBr method) is shown in FIG. 2.

$_{max}$=2930$^m$, 1590$^s$, 1025$^w$cm$^{-1}$.

UV absorption spectrum; max=(H$_2$O), 210, 267 nm (0.1 N-HC), 273 nm (0.1 N-NaOH), 274 nm, 284$^{sh}$nm.

EXAMPLE 3

Preparation of N$^6$-[2-(N-methoxy-N-methylamino)-butyl]adenine of the formula (4):

First, a side chain amine was prepared and then was allowed to react with 6-chloropurine in the following manner.

(1) Preparation of N$^6$-[2-(N-methoxy-N-methylamino)butyl]phthalimide:

To a suspension of 50 ml of isopropanol containing N,O-dimethylhydroxylamine hydrochloride (3.97 g, 40.0 mmol) was added dropwise 5.56 ml of triethylamine. The resulting mixture became homogeneous after 5 minutes. There were added 2.00 g (7.09 mmol) of N-(4-bromobutyl)phthalimide and the mixture was refluxed for 58 hours. This was cooled to room temperature, then poured into 200 ml of saturated aqueous solution of sodium bicarbonate and extracted with chloroform. The organic layer was separated, was washed with water and dried over magnesium sulfate. Chloroform was distilled off and the residue was purified by column chromatography on silica gel. Development with 30% hexane-chloroform resulted in elution of 0.719 g of N-(4-chlorobutyl)-phthalimide and further development with chloroform resulted in 0.964 g (yield: 41%) of N-[4-(N-methoxy-N-methylamino)-butyl]phthalimide as an oil.

$^1$H-NMR (60 MHz, CDC$_3$); =1.66 (m, 4H), 2.56 (s, 3H), 2.62 (t, J=7H$_z$, 2H), 3.17 (s, 4H), 3.73 (t, J-7H$_z$, 2H), (2) Preparation of N$^6$-[4-(N-methoxy-N-methylamino)-butyl]adenine by deprotection of the imide, followed by condensation with 6-chloropurine:

In 15 ml of ethanol, were dissolved 1.01 g (3.85 mmol) of the imide obtained in the above (1) and there were added 0.231 g (4.06 mmol) of hydrazine hydrate, followed by refluxing for 6 hours and cooling in an ice bath. The resulting solid was filtered off and the filtrate was concentrated to 2 ml by an evaporator with a water bath at 5° C. This solution was mixed with 10 ml of n-butanol and to the mixture were added 0.357 g (2.31 mmol) of 6-chloropurine and 0.67 ml of ethyldiisopropylamine and the mixture was gently refluxed for 6 hours. This was cooled to room temperature and then the solvent was distilled off under reduced pressure. The residue was purified by column chromatography on silica gel (eluent: chloroform/ethanol=88/12) to give 0.299 g (yield: 31%) of white cyrstals of N$^6$-[4-(N-methoxy-N-methylamino)butyl]adenine.

Melting point: 181°–184° C.

Elemental analysis: Molecular formula: C$_{11}$H$_{18}$N$_6$O; Calculated values: C; 52.78, H; 7.25, N; 33.58; Found: C; 52.91, H; 7.20, N; 33.42.

Figure 3:
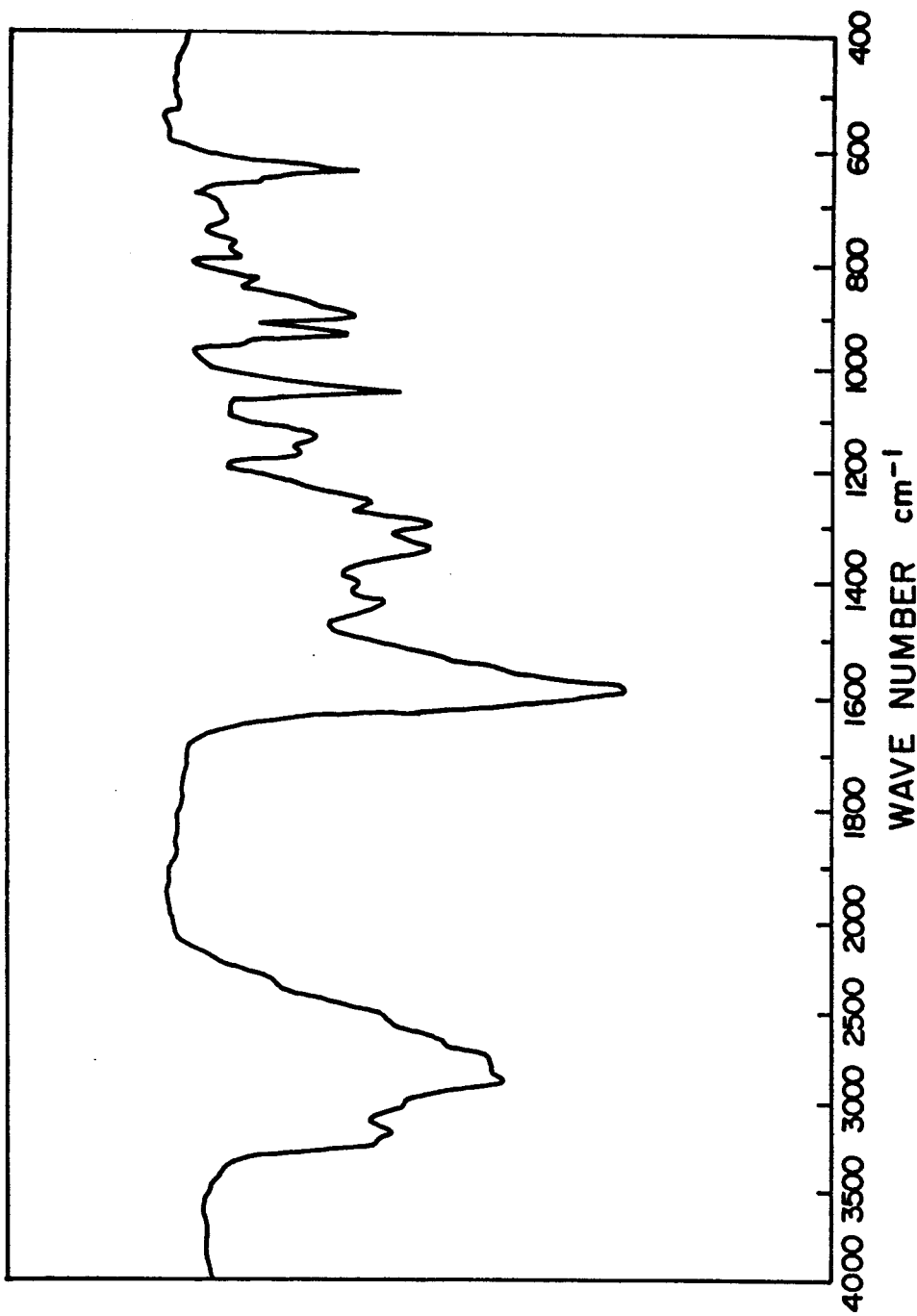

$^1$H-NMR (60MH$_z$, CDC$_3$); =1.74 (m, 4H), 2.55 (s, 3H), 2.65 (t, J=6H$_z$, 2H), 3.47 (s, 3H), 3.75 (m, 2H), 6.38 (t, J=6H$_z$, 1H), 7.88 (m, 1H), 8.32 (s, 1H) ppm, IR absorption spectrum (KBr method) is shown in FIG. 3.

$_{max}$=2930$^s$, 1590$^s$, 1035$^m$cm$^{-1}$.

UV absorption spectrum; max=(H$_2$O), 210, 269 nm (0.1 N-HC), 273 nm.

EXAMPLE 4

Preparation of N$^6$-[2-(N-methoxy-N-methylamino)ethyl]adenine hydrochloride:

In 30 ml of ethanol was dissolved 0.44 g (2 mmol) of N$^6$-[2-(N-methoxy-N-methylamino)ethyl]adenine and this solution was mixed with 0.2 g (2mmol) of 36% hydrochloric acid. The solvent was distilled off and the residual crystals were washed thrice with 5 ml of a mixed solvent of methanol and ethanol (5:95) and dried to give 0.48 g (yield: 93%) of the hydrochloride salt of N$^6$-[2-(N-methoxy-N-methylamino)ethyl]adenine.

Melting point: 172°–176° C.

Elemental analysis: Molecular formula: C$_9$H$_{15}$N$_6$ClO; Calculated values: C; 41.78%, H; 5.84%, N; 32.48% Cl; 13.70%; Found: C; 41.49%, H; 5.77%, N; 32.59% Cl; 13.56%

$^1$H-NMR (90 MHz, DMSO); =2.66 (s, 3H), 3.03 (t, J=6H$_z$, 2H), 3.55 (s, 3H), 3.86 (m, 2H), 8.69 (s, 2H) ppm.

Figure 4:
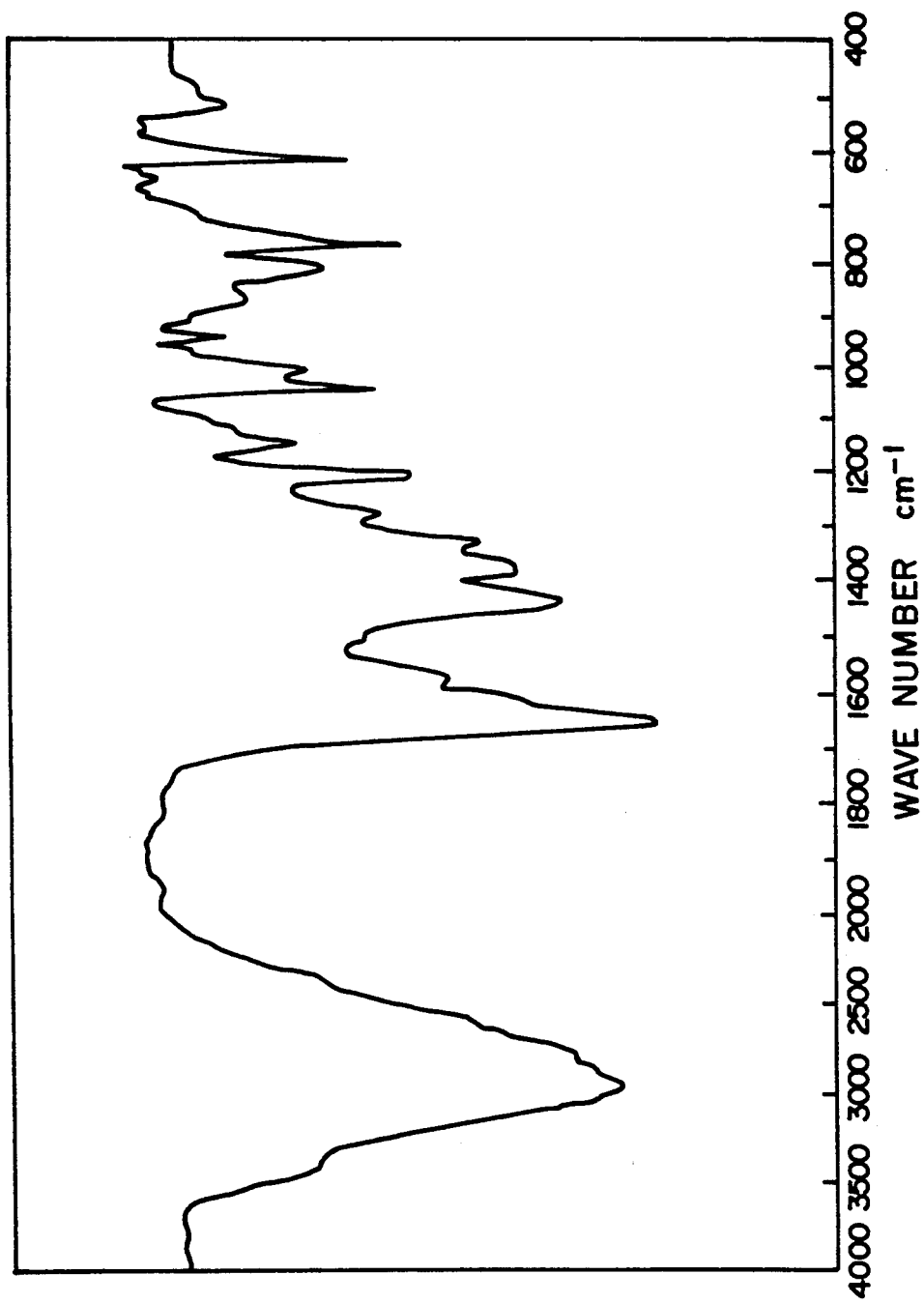
FIG. 4 shows the IR absorption spectrum of N6-[2-(N-methoxy-N-methylamino)ethyl]adenine hydrochloride of the present invention.

IR absorption spectrum (KBr method) is shown in FIG. 4.

$_{max}$=2950$^{brs}$, 1650$^s$, 1440$^s$cm$^{-1}$.

UV absorption spectrum; max=(H$_2$O), 210, 268 nm (0.1 N-HC), 275 nm (0.1 N-NaOH), 274 nm, 282$^{sh}$cm$^{-1}$.

EXAMPLE 5

Assay of Cytokinin Activity by Measurement of Chlorophyll Content

Rice seeds (var.: Nankin No. 11) were sown in soil mixed with fertilizer filled in a seed box and raised for about one month in a greenhouse (25° C. in the daytime and 15° C. in the night).

A leaf section of 1 cm long was cut from the center of the fourth leaf of the seedlings at the sixth leaf stage. Five leaf sections as one group which had been cut off were floated on the surface of an aqueous solution (2 ml) of the candidate compound or benzyladenine at a given concentration poured in a glass tubular bottle of 32 mm in inner diameter. This was left to stand in the dark at 30° C. for 3 days. The leaf sections were taken out and put in a test tube containing 10 ml of 80% ethanol and the glass tube was immersed in a water bath of 80° C. for 20 minutes to extract chlorophyll. After cooling, 80% ethanol was added to make up to 10 ml and absorbance at 665 nm was measured. The results are shown in Table 1. For untreated group, water was used in place of the candidate solution in all examples.

Senescence retardation was determined according to the degree of chlorophyll retention, that is, calculated by the following formula (in all examples).

$$\text{Senescence retardation (\%)} = \frac{(A) - (B)}{(C) - (B)} \times 100$$

(A): Absorbance of treated group after 3 days
(B): Absorbance of untreated group after 3 days
(C): Absorbance of leaves before treatment

TABLE 1

| The senescence retardation (%) of adenine derivatives | | | | | | |
|---|---|---|---|---|---|---|
| Concentration (mg/l) | 0.001 | 0.01 | 0.1 | 1.0 | 10 | 100 |
| MAED | 14 | 60 | 100 | 95 | — | — |
| MAPD | — | 18 | 50 | 94 | 99 | 91 |
| MABD | — | 1 | 11 | 21 | 77 | 87 |
| Benzyladenine | 17 | 64 | 93 | 93 | — | — |

MAED: $N^6$-[2-(N-methoxy-N-methylamino)ethyl]adenine
MAPD: $N^6$-[3-(N-methoxy-N-methylamino)propyl]adenine
MABD: $N^6$-[2-(N-methoxy-N-methylamino)ethyl]adenine
(These are the same in all of the following examples.)

EXAMPLE 6

Assay for cytokinin activity according to glycine (soybean) hypocotyl section growth test Soybean seeds (var.: Enrei) were disinfected with antiformin containing 0.7% effective chlorine for 4 minutes and washed thrice with sterilized water.

Agar (15 ml, 1.6%) was put in a test tube of 2.5 cm in diameter. A groove was cut by a forceps on the surface of the agar and two soybean seeds treated as above were placed in this groove and kept in the dark at 30° C. for 5 days.

In a glass tubular bottle of 26 mm in inner diameter was put a Miller's medium, to which a given concentration of the candidate compound, benzyladenine or zeatin and 9 mg/l of 2,4-D were added. The central portion of hypocotyl budding out from the above seeds was cut off to give a section of 1 mm thick. Four of the sections as one group were transplanted to the Miller's medium. This was placed in the dark at 30° C. for about one month and then the weight of the callus formed was measured. For untreated group, the Miller's medium containing 9 mg/l of 2,4-D was used.

TABLE 2

| The weight of soybean callus formed (mg) | | | | | | |
|---|---|---|---|---|---|---|
| Concentration (mg/l) | 0 | 0.001 | 0.01 | 0.1 | 1.0 | 10 |
| MAED | — | 97 | 182 | 654 | 823 | 705 |
| MAPD | — | — | 131 | 143 | 841 | 677 |
| MABD | — | — | 51 | 152 | 178 | 824 |
| Benzyladenine | — | 76 | 836 | 674 | — | — |
| t-Zeatin | — | 52 | 382 | 815 | 662 | — |
| Untreated | 22 | — | — | — | — | — |

EXAMPLE 7

Assay of cytokinin activity to promote synthesis of batacyanin of pig weed (*Amaranthus caudatus*)

Two sheets of filter paper were put double in a plastic container (19×28 cm) and were wetted with 60 ml of distilled water. Seeds of pig weed were sown on the filter papers and were germinated by keeping them in the dark at 27° C. for 3 days. Seedlings of uniform size were chosen and were cut at upper part of hypocotyl and seed coats were removed. This cotyledon with hypocotyl of 3–4 mm in length was used for assay.

Two sheets of filter paper were put double in a glass tubular bottle of 32 mm in inner diameter and 1 ml of 0.0065M potassium phosphate buffer solution (pH: 6.3) containing a given concentration of the candidate compound, benzyladenine or zeatin and 0.5 g/l of tyrosine was added therein, and ten of the above cotyledon sections were arranged therein and kept at 27° C. for 20 hours in the dark. These ten cotyledon sections were put in a test tube containing 3 ml of distilled water and betacyanin was extracted by repeating thrice freezing and thawing. Absorbance of the solution was measured and the amount of the dye was calculated by the difference between the absorbance at 542 nm and 620 nm. For untreated group, 0.0065M potassium phosphate buffer solution (pH: 6.3) containing 0.5 g/l of tyrosine was used. The results are shown in Table 3.

TABLE 3

| The amount of betacyanin produced (difference between absorbance at 542 nm and 620 nm) | | | | | | | |
|---|---|---|---|---|---|---|---|
| Concentration (mg/l) | 0 | 0.001 | 0.01 | 0.1 | 1.0 | 10 | 100 |
| MAED | — | 0.040 | 0.058 | 0.121 | 0.214 | — | — |
| MAPD | — | — | — | 0.065 | 0.132 | 0.227 | 0.236 |
| MABD | — | — | — | 0.044 | 0.069 | 0.127 | 0.207 |
| Benzyladenine | — | 0.038 | 0.076 | 0.192 | 0.260 | — | — |
| t-Zeatin | — | 0.040 | 0.062 | 0.198 | 0.242 | — | — |
| Untreated | 0.037 | — | — | — | — | — | — |

EXAMPLE 8

Assay for absorption and translocation using wheat (1) Comparison of activity of MAED and benzyladenine on leaf section of wheat:

Seeds of wheat [var.: Yukichabo (triticum astivum)] were sown in vermiculite packed in a seed-bed box and were sprouted by keeping them at 28° C. for 2 days in the dark. The seedlings were grown at 25° C. for 5 days under irradiation of light of 1500 Lx. When they grew to a length of 12–13 cm, a portion of 2–5 cm from the tip of the first true leaf was cut off in a length of 1 cm. Five of the leaf sections as one group were floated with the upper surface of the leaf being upward on aqueous solution (2 ml) of a given concentration of the candidate compound or benzyladenine contained in a glass tubular bottle of 32 mm in inner diameter. These were placed at 25° C. for 4 days in the dark and thereafter, these leaf sections were put in a test tube containing 10 ml of 80% ethanol and this test tube was immersed in a water bath of 80° C. for 20 minutes to extract chlorophyll. After cooling, 80% ethanol was added to make up to 10 ml and absorbance at 665 nm was measured. Senescence retardation was determined according to the degree of retention of chlorophyll. For untreated group, water was used in place of the aqueous solution of candidate compound. The results are shown in Table 4.

TABLE 4

| The senescence retardation (%) of adenine derivatives | | | | | | |
|---|---|---|---|---|---|---|
| Concentration (mg/l) | 0.0001 | 0.001 | 0.01 | 0.1 | 1.0 | 10 |
| MAED | 4 | 14 | 43 | 56 | 58 | 76 |
| Benzyladenine | 7 | 15 | 50 | 55 | 74 | 75 |

(2) Absorption of adenine derivatives from the surface of leaf of wheat and translocation thereof:

In the same manner as in the above (1), wheat seedlings were grown to a height of 12–13 cm and a portion of 4 cm from tip of the first true leaf was cut off and this leaf section was used for this test.

The bottom of a Petri dish of 9 cm in diameter was covered with a sheet of circular filter paper which was wetted with 2.5 ml of distilled water. A slide glass was put theron and ten of the leaf sections were arranged on this slide glass with the upper surface of the leaf being upward. On the center of the leaf sections was put 10 ul of the solution prepared by dissolving the candidate compound or benzyladenine in 0.2% aqueous solution of Tween 80 at a given concentration. The Petri dish was covered and left at 25° C. for 5 days in the dark. In the part where the candidate solution was absorbed and translocation around the position on which the solution was put, the length of the portion where chlorophyll was retained, namely, the length of the green portion was measured. The results are shown in Table 5. At same concentration, MAED expanded the green portion in more widely than benzyladenine and this means that MAED is superior in absorbability and translocation.

TABLE 5

| The length of the green portion (mm) (average in 10 leaves) | | | |
|---|---|---|---|
| concentration (mg/l) | 0.1 | 1.0 | 10 |
| MAED | 9.9 | 19.8 | 28.8 |
| Benzyladenine | 9.6 | 14.2 | 16.9 |

(3) Absorption of adenine derivatives from the base of wheat and translocation thereof:

Wheat seedlings were grown to a height of 14–15 cm in the same manner as in the above test (1) and shoot of them was cut off at the base. These sections were used for the test.

A solution (10 ml) containing 10 mg/l of the candidate compound or benzyladenine was poured in a test tube of 2.5 cm in diameter and five of the wheat shoots as one group were inserted in one test tube containing the candidate solution and left at 25° C. for 18 hours under irradiation of light of 1500 Lx. Thereafter, each of the shoots was cut at 5–6 cm, 8–9 cm and 11–12 cm from the above cut end and five of the respective sections as one group were floated on the surface of distilled water (2 ml) in a glass tubular bottle of 32 mm in inner diameter with the upper surface of leaves being upward. These were left at 25° C. for 3 days in the dark and thereafter, the leaf sections were put in a test tube containing 10 ml of 80% ethanol. This test tube was immersed in a water bath of 80° C. for 20 minutes to extract chlorophyll. After cooling, 80% ethanol was added to make up to 10 ml and absorbance of the solution at 665 nm was measured. In the same manner as in the above (1), senescence retardation was obtained. The results are shown in Table 6.

TABLE 6

| The senescence retardation (%) of adenine derivatives | | | |
|---|---|---|---|
| Region of leaf section | 5–6 (cm) | 8–9 (cm) | 11–12 (cm) |
| MAED | 37 | 34 | 20 |
| Benzyladenine | 17 | 21 | 14 |

It can be seen from Table 6 that MAED showed more pronounced effect of senescence retardation than that of benzyladenine in all regions of the first true leaf of wheat and thus MAED has superior absorbability and translocation.

EXAMPLE 9

Test on Effect to Promote Photosynthesis

Figure 5:
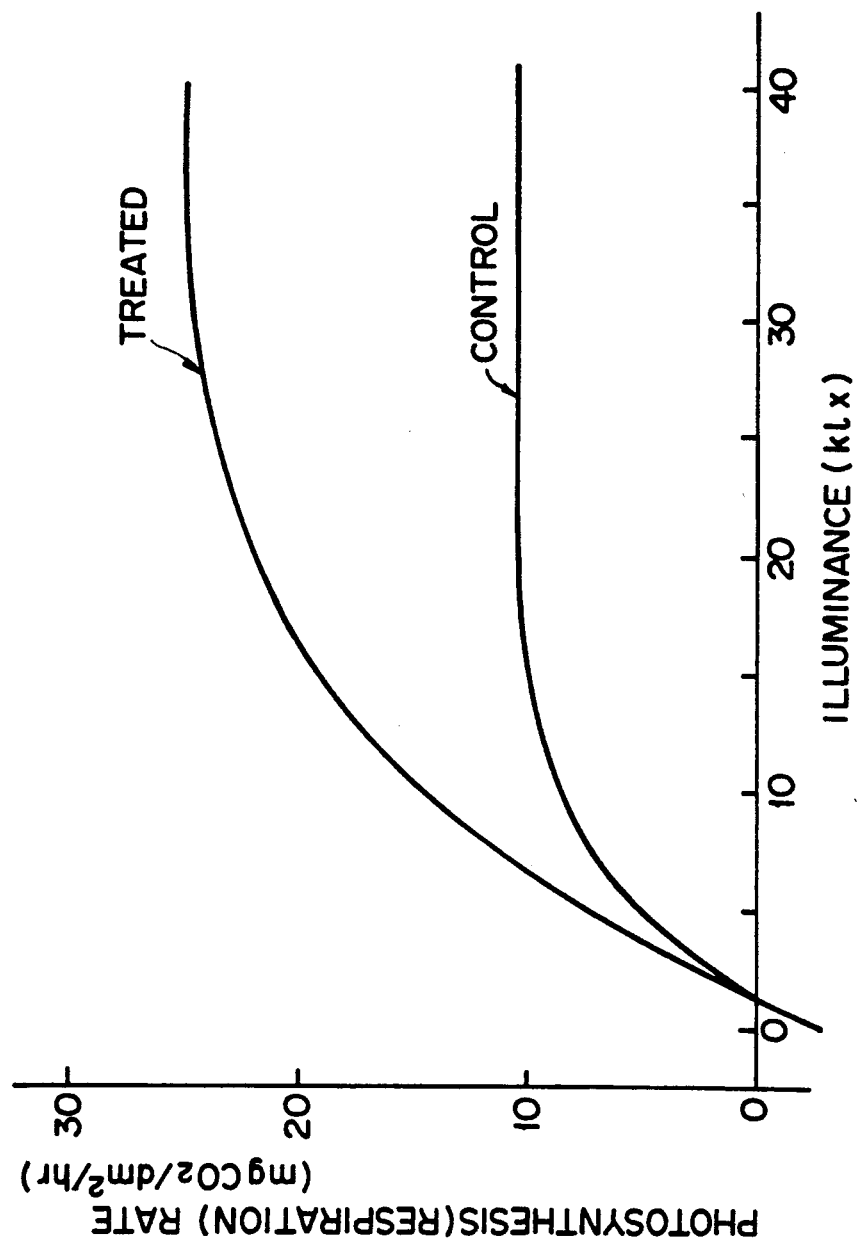
FIG. 5 is a graph which shows $CO_2$ absorption rate of $N^6$-[2-(N-methoxy-N-methylamino)ethyl]adenine of the present invention.

Soybean (var.: Enrei) were sown in a pot and raised in a phytotron under natural light set at 25° C. in the daytime and 20° C. in the night and 70–80% in humidity. The seedlings at the fourth leaf stage (34th day after sown) were subjected to application with an aqueous solution containing 1 ppm of MAED and 200 ppm of TWEEN 20 as a surface-active agent in such a manner that the surface of leaf was wetted. On 30th day after application, the third leaf was subjected to measurement of photosynthetic rate by $CO_2$ measuring method using an assimilation box. Absorption rate of $CO_2$ is shown in FIG. 5.

EXAMPLE 10

Water solubility of adenine derivatives of the invention was measured and the results are shown in Table 7. As shown in Table 7, the adenine derivatives of the present invention show far higher solubility than the known cytokinin substances.

TABLE 7

| Substances | Solubility (g/100 g $H_2O$) (20° C.) |
|---|---|
| MAED | 9.9 |
| MAPD | 13.6 |
| MABD | 5.3 |
| Benzyladenine | $3 \times 10^{-3}$ |
| t-Zeatin | 0.14 |
| Kinetin | $2 \times 10^{-3}$ |

EXAMPLE 11

A liquid formulation was prepared by dissolving 0.1 g MAED and 10.0 g of SORPOL-8222 (nonionic surface-active agent manufactured by Toho Chemical Co., Ltd.) in 89.9 g of water.

EXAMPLE 12

An emulsifiable concentrate was prepared by dissolving 2 g of MAED and 38 g of AEROL CT-1 (anionic surface-active agent manufactured by Toho Chemical Co., Ltd.) in 60 g of dimethyl sulfoxide.

EXAMPLE 13

A wettable powder was prepared by pulverizing 10 g of MAED, 15 g of white carbon, 3 g of calcium lignin sulfonate, 1 g of polyoxyethlenenonylphenyl ether, 5 tg of diatomaceous earth, and 66 g of clay and homogeneously mixing them.

EXAMPLE 14

Young seedlings of rice (var.: Koshihikari) were planted in a paddy field on April 20th. The MAED liquid formulation prepared in Example 11 was diluted with water to the given concentrations as shown in Table 8 and 100l/10a of each solution was applied to leaves and stems on August 4th at the boot stage and on August 19th at the initial ripening stage (the tenth day after heading), respectively.

As a comparative example, an emulsifiable concentrate (hereinafter referred to as "BA emulsifiable concentrate") was prepared by dissolving 2 g of benzyladenine and 38 g of AEROL CT-1 (the aninonic surface-active agent manufactured by Toho Chemical Co., Ltd.) in 60 g of dimethyl-sulfoxide was applied at the same stage in the same concentration with the same total amount as in application of the MMEA liquid formulation conducted.

One experimental plot had an area of 6 m² and three plots were used for each treatment. The rice plants were harvested on September 19th which corresponded to the 41th day after heading and the husked rice weight and thousand-kernel weight of husked rice were measured.

The results are shown in Table 8.

TABLE 8

| Chemicals | Treating stage | Concentration (ppm) | Husked rice weight (ratio to untreated rice) (%) | Thousand-kernel weight of husked rice (ratio to untreated rice) (%) |
|---|---|---|---|---|
| MAED liquid formulation | Boot stage | 0.3 | 105 | 101 |
| | | 1 | 108 | 102 |
| | | 3 | 109 | 102 |
| | Tenth day after heading | 0.3 | 108 | 102 |
| | | 1 | 110 | 103 |
| | | 3 | 109 | 102 |
| BA emulsifiable concentrate | Boot stage | 0.3 | 100 | 100 |
| | | 1 | 102 | 100 |
| | | 3 | 103 | 100 |
| | Tenth day after heading | 0.3 | 100 | 100 |
| | | 1 | 103 | 100 |
| | | 3 | 104 | 101 |
| Untreated | — | | 100 | 100 |

Husked rice weight of untreated section was 536 kg/10a and thousand-kernel weight of husked rice was 21.0 g.

EXAMPLE 15

Seeds of winter wheat (var.: Norin No. 61) were sown in a field on October 20th and leaves and stems were subjected to application with 100l/10a of the diluted MMEA liquid formulation and the diluted BA emulsifiable concentrate as a comparable example, prepared in the same manner as in Example 14, on April 20th corresponding to the most growing stage and on May 10th corresponding to the initial ripening stage, respectively.

On 235th day after sowing, crops were harvested and the grain weight was measured.

The results are shown in Table 9.

TABLE 9

| Chemicals | Treating stage | Concentration (ppm) | Grain weight (ratio to untreated ones) (%) |
|---|---|---|---|
| MAED liquid formulation | The most growing stage | 0.1 | 111 |
| | | 0.3 | 110 |
| | | 1 | 116 |
| | The initial ripening stage | 0.1 | 117 |
| | | 0.3 | 119 |
| | | 1 | 110 |
| BA emulsifiable concentrate | The most growing stage | 0.1 | 100 |
| | | 0.3 | 100 |
| | | 1 | 103 |
| | The initial ripening stage | 0.1 | 100 |
| | | 0.3 | 104 |
| | | 1 | 105 |
| Untreated | — | — | 100 |

Grain weight per 10a of untreated group was 470 kg.

EXAMPLE 16

Seeds of soybean (var.: Enrei) were sown in a field on May 15th and leaves and stems were subjected to application with 100l/10a of the diluted MMEA liquid formulation and the diluted emulsifiable concentrates as a comparable example, prepared in the same manner as in Example 14, on July 3rd corresponding to the beginning of flowering and on August 7th corresponding to the initial ripening stage, respectively.

One experimental plot had an area of 12 m² and four replicate plots were used for each treatment. On 132nd day after sowing, crops were harvested and the grain weight was measured.

The results are shown in Table 10.

TABLE 10

| Chemicals | Treating stage | Concentration (ppm) | Grain weight (ratio to untreated ones) (%) |
|---|---|---|---|
| MAED liquid formulation | The beginning of flowering | 0.3 | 110 |
| | | 1 | 116 |
| | The initial ripening stage | 0.3 | 107 |
| | | 1 | 112 |
| BA emulsifiable concentrate | The beginning of flowering | 0.3 | 102 |
| | | 1 | 104 |
| | The initial ripening stage | 0.3 | 103 |
| | | 1 | 103 |
| Untreated | — | — | 100 |

Grain weight per 10a of untreated group was 372 kg.

We claim:

1. Adenine derivatives represented by the formula:

$$\text{NH(CH}_2\text{)n}-\overset{\text{CH}_3}{\underset{|}{\text{N}}}-\text{OCH}_3$$

(attached to adenine ring system)

wherein n is an integer of 2-4 and agriculturally acceptable acid addition salts thereof.

2. An adenine derivative according to claim 1 which is represented by the formula:

[Structure: 6-(N-methoxy-N-methylamino-ethylamino)-purine]

and agriculturally acceptable acid addition salts thereof.

3. An adenine derivative according to claim 1 which is represented by the formula:

[Structure: 6-(3-(N-methoxy-N-methylamino)propylamino)-purine]

and agriculturally acceptable acid addition salts thereof.

4. An adenine derivative according to claim 1 which is represented by the formula:

[Structure: 6-(4-(N-methoxy-N-methylamino)butylamino)-purine]

and agriculturally acceptable acid addition salts thereof.

5. An adenine derivative according to any one of claims 1 to 4, wherein the agriculturally acceptable salt is hydrochloric acid, sulfuric acid, nitric acid, phosphoric acid, formic acid or acetic acid.

6. The adenine derivative represented by the formula:

[Structure: 6-(2-(N-methoxy-N-methylamino)ethylamino)-purine · HCl]

7. A composition for increasing yield of crops which contains an agriculturally acceptable carrier and, as an active ingredient, an effective amount of an adenine derivative represented by the formula:

[Structure with NH(CH$_2$)n group]

wherein n is an integer of 2–4 or agriculturally acceptable acid addition salts thereof.

8. A composition in claim 7 wherein the adenine derivative is represented by the formula:

[Structure]

ps or agriculturally acceptable acid addition salts thereof.

9. A composition according to claim 7 or 8 wherein the agriculturally acceptable acid is hydrochloric acid, sulfuric acid, nitric acid, phosphoric acid, formic acid, or acetic acid.

10. A composition according to claim 7, 8 or 9 wherein the agriculturally acceptable acid is represented by the formula:

[Structure · HCl]

11. A composition according to claim 7, 8, 9 or the carrier is a liquid.

12. A composition according to claim 7, 8, 9 or 10 wherein the carrier is a solid.

13. A method for increasing yield of crops, which comprises applying an adenine derivative of claim 1 to crops to be treated.

14. A method according to claim 11 which comprises applying the adenine derivative to leaves and stems of leguminous crops or gramineous crops.

15. A method according to claim 14 wherein the dosage of the adenine derivative is 0.03–3 g/10a.

16. A method according to claim 13 which comprises applying the adenine derivative to leguminous crops during the period of from the flower bud appearing stage to the grain ripening stage.

17. A method according to claim 13 which comprises applying the adenine derivative to gramineous crops during the period of the panicle formation stage to the ripening stage.

* * * * *